US00PP13878P39

(12) United States Plant Patent
Swartz et al.

(10) Patent No.: US PP13,878 P3
(45) Date of Patent: Jun. 17, 2003

(54) BLACKBERRY PLANT NAMED 'CHESAPEAKE'

(75) Inventors: Harry J. Swartz, Laurel, MD (US); Joseph A. Fiola, Keedysville, MD (US); Herbert D. Stiles, Blackstone, VA (US); Brian R. Smith, River Falls, WI (US)

(73) Assignees: University of Maryland, College Park, MD (US); Virginia Tech Intellectual Properties, Inc., Blacksburg, VA (US)

( * ) Notice: Subject to any disclaimer, the term of this patent is extended or adjusted under 35 U.S.C. 154(b) by 0 days.

(21) Appl. No.: 09/917,242

(22) Filed: Jul. 30, 2001

(65) Prior Publication Data

US 2003/0024021 P1 Jan. 30, 2003

(51) Int. Cl.[7] ..... A01H 5/00

(52) U.S. Cl. ..... Plt./203

(58) Field of Search ..... Plt./203

*Primary Examiner*—Bruce R. Campell
*Assistant Examiner*—June Hwu
(74) *Attorney, Agent, or Firm*—James A. Poulos, III

(57) ABSTRACT

The present invention is a new and distinct thorny blackberry cultivar named 'Chesapeake', which is capable of producing very large fruit in the spring midseason, the fruit being much larger and similarly durable than that of the standard cultivars. The cultivar is characterized by moderate suckering ability, recurved thorns and its very flavorful fruit which is edible even when the fruit is immature.

7 Drawing Sheets

GENUS AND SPECIES OF THE CLAIMED PLANT

Rubus hybrid.

VARIETY DENOMINATION

'Chesapeake'.

FIELD OF THE INVENTION

This invention concerns a new and distinct cultivar of thorny blackberry plant with a botanical name of *Rubus argutus*×*R. cuneifolius L.*

DESCRIPTION OF RELATED PRIOR ART

Several cultivars of thorny blackberry plants are known. 'Chesapeake' may be distinguished from its parent, 'Shawnee' (U.S. Plant Pat. No. 5,686) and other large fruited thorny blackberry cultivars such as 'Kiowa' (U.S. Plant Pat. No. 9,861) by the recurvature of its spines and flavor of its fruit. It may be distinguished from 'Black Butte' (unpatented) by the type of spines and its erectness, compared to the semi trailing habit of the large fruited 'Black Butte'. Fruit size and flavor distinguishes 'Chesapeake' from all other thorny blackberry cultivars known to us, including 'Choctaw' (U.S. Plant Pat. No. 6,678), 'Illini Hardy' (U.S. Plant Pat. No. 8,333), 'Raven' (unpatented) and 'Ranger' (unpatented). The presence of thorns and the size of the fruit distinguish 'Chesapeake' from thornless cultivars such as 'Arapaho' (U.S. Plant Pat. No. 8,510), 'Navaho' (U.S. Plant Pat. No. 6,679), 'Hull Thornless' (unpatented), 'Triple Crown' (unpatented) and 'Chester Thornless' (unpatented).

ORIGIN OF THE NEW CULTIVAR

The new cultivar of blackberry originated from a controlled cross at the University of Maryland Greenhouses in College Park, Md. The cross "SKNA" was 'Shawnee' (U.S. Plant Pat. No 5,686)×*R. cunefolius* (a wild selection from the town of Crisfeld, Md). This year was designated "N" as part of the University of Maryland at College Park; Rutgers University of New Brunswick, N.J.; Virginia Polytechnic Institute and State University, Southern Piedmont Agricultural Research and Education Center at Blackstone; and the University of Wisconsin at River Falls cooperative breeding program. The clone was first selected in 1992 at the Wye Research and Education Center of the University of Maryland located at Centerville, Md. and was therefore designated "−1". Thus, the complete breeding designation was "NSKNA-1".

SUMMARY OF THE NEW CULTIVAR

This application relates to a new and distinct thorny, spring bearing blackberry cultivar, botanically known as *Rubus argutus*×*R. cuneifolius L.* The following characteristics are outstanding:

1. Production of fruit which is much larger than the standard cultivars in use and larger or of equal size to two new extra large cultivars, 'Black Butte' (unpatented) and 'Kiowa' (U.S. Plant Pat. No. 9,861).

2. When compared to all othern eastern blackberry cultivars known to us, 'Chesapeake' has production of fruit which have a flavor less acid when slightly immature, at the glossy black fruit stage, allowing a slight blueberry flavor to emerge.

The following characteristics are useful in distinguishing this cultivar and can be useful for cultivar identification.

1. Plants are sparingly suckering and very upright, growing to 12 feet or taller when mature. Canes are only moderately cold hardy, i.e. not recommended for areas where the minimum winter temperature is less than 0° F.

2. Canes, petioles, petiolules and leaf midribs have only a moderate amount of large recurved thorns.

3. The fruit is very large, typically 15–22 grams in the first picking and has an aroma of a blueberry in cooler temperatures. The flavor contains undetectable quantities of highly aromatic compounds typical of eastern U.S. erect thorny or semierect thornless blackberry cultivars.

4. The fruit is produced in the midseason from floricanes. Primocane produced fruit is unknown.

BRIEF DESCRIPTION OF THE PHOTOGRAPHS

The accompanying photographs show typical characteristics of the new variety:

DESCRIPTION OF THE NEW CULTIVAR

The following is a detailed description of the new cultivar, together with the cultivar's morphological characteristics. The characteristics of the cultivar were compared to other standards used in the Mid-Atlantic Region of the U.S. and a parent, 'Shawnee' (U.S. Plant Pat. No. 5,686). The description is based on information provided by cooperating growers and scientists from plants grown in fields at Cream Ridge and Colt's Neck, N.J., Millersville, Pa., and Oak Grove, Va., and from plants grown in the University of Maryland greenhouses at College Park, Md.

Figure 1:
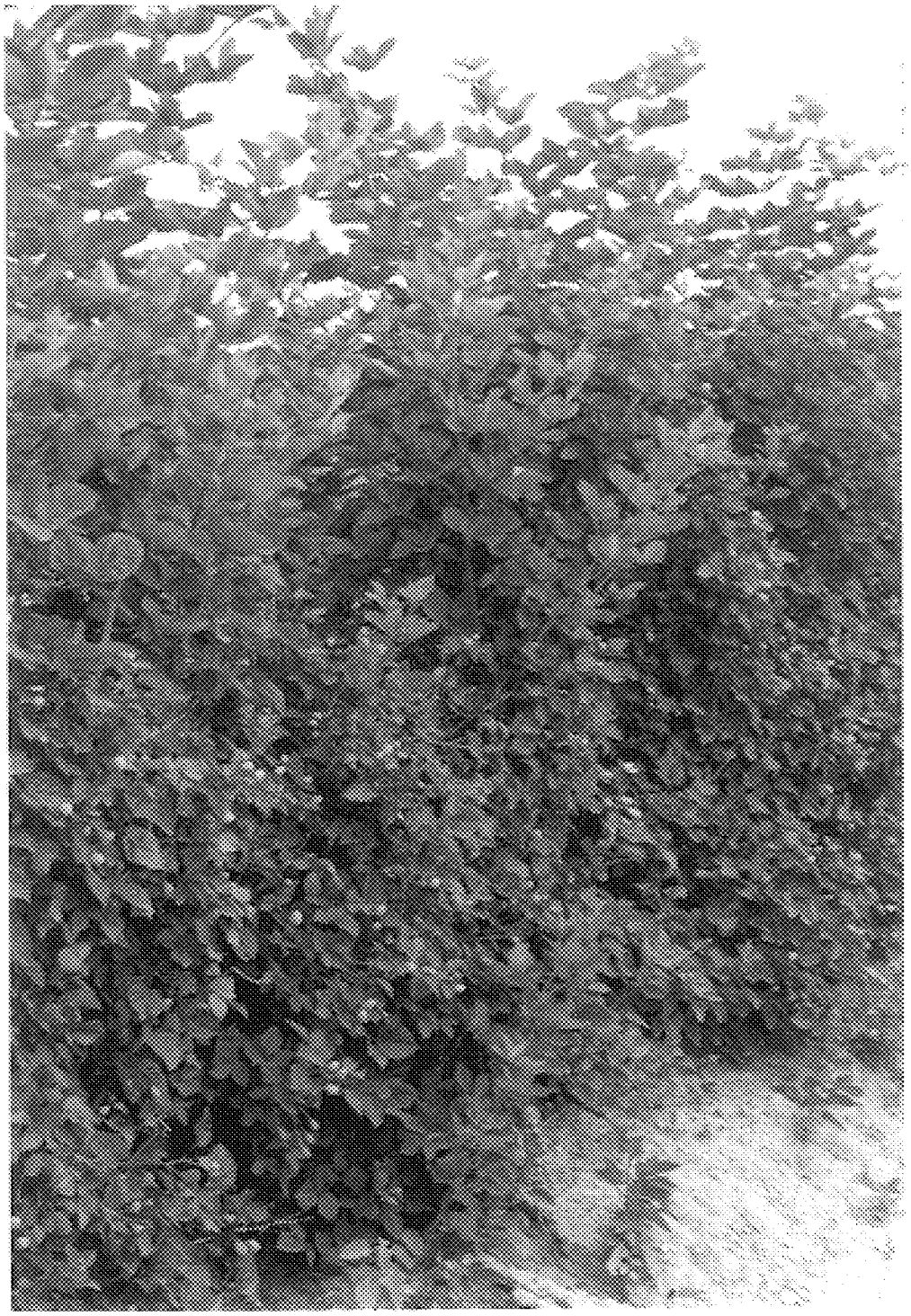
FIG. 1 shows a young 'Chesapeake' plant in July 2000, the primocane height is 6 feet. The plants are in their second growing season in Millersville, Pa.

'Chesapeake' produces a moderate number of root-and crown-suckers, typically 2.7 per plant or 13 per 10 foot of row as measured on 3 year old plants in Colt's Neck, N.J., similar to 'Shawnee' (U.S. Plant Pat. No. 5,686) and other thorny blackberry cultivars tested or grown in the eastern United States. It can therefore be trained as a hedgerow or maintained as individual plants. During the growing season, primocanes are light green colored (Royal Horticultural Society plate 143B vs. 146B for 'Shawnee') with a light red blush (Royal Horticultural Society plate 59A) in full sun, fluted or moderately grooved, usually branched, very erect with arching branches and very vigorous (see FIG. 1). In Beltsville, Md. (in full sun), average cane diameter at 10 cm height is 11.8 mm and average internode length in the bottom 50 cm of the canes is 325 cm. Floricanes are not noticably exfoliating, with only an occasional narrow split. Floricane color is brown (Royal Horticultural Society plate 178A).

Figure 2:
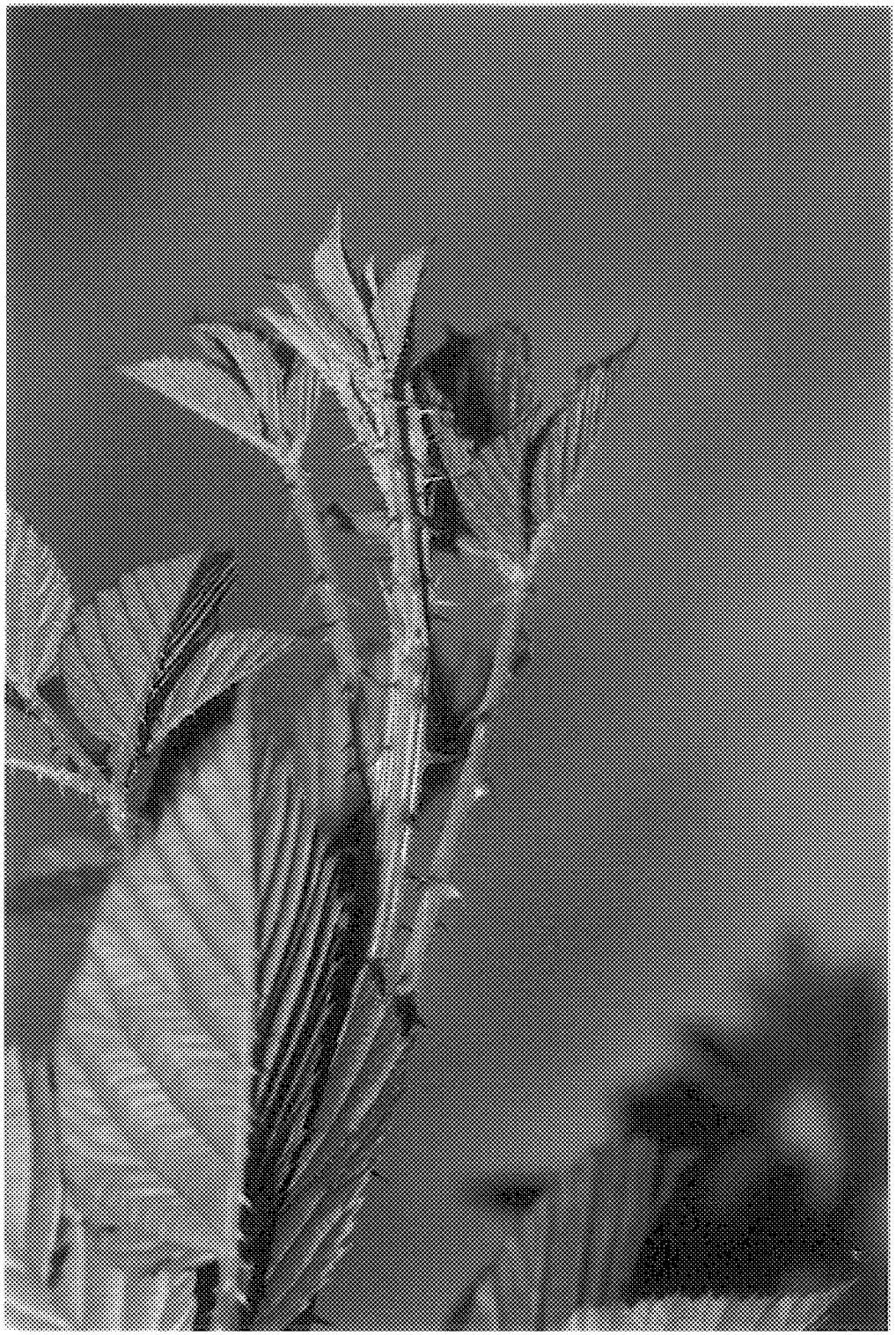
FIG. 2 shows the type and density of thorns on the apex of a fluted 'Chesapeake' primocane.
Figure 3:
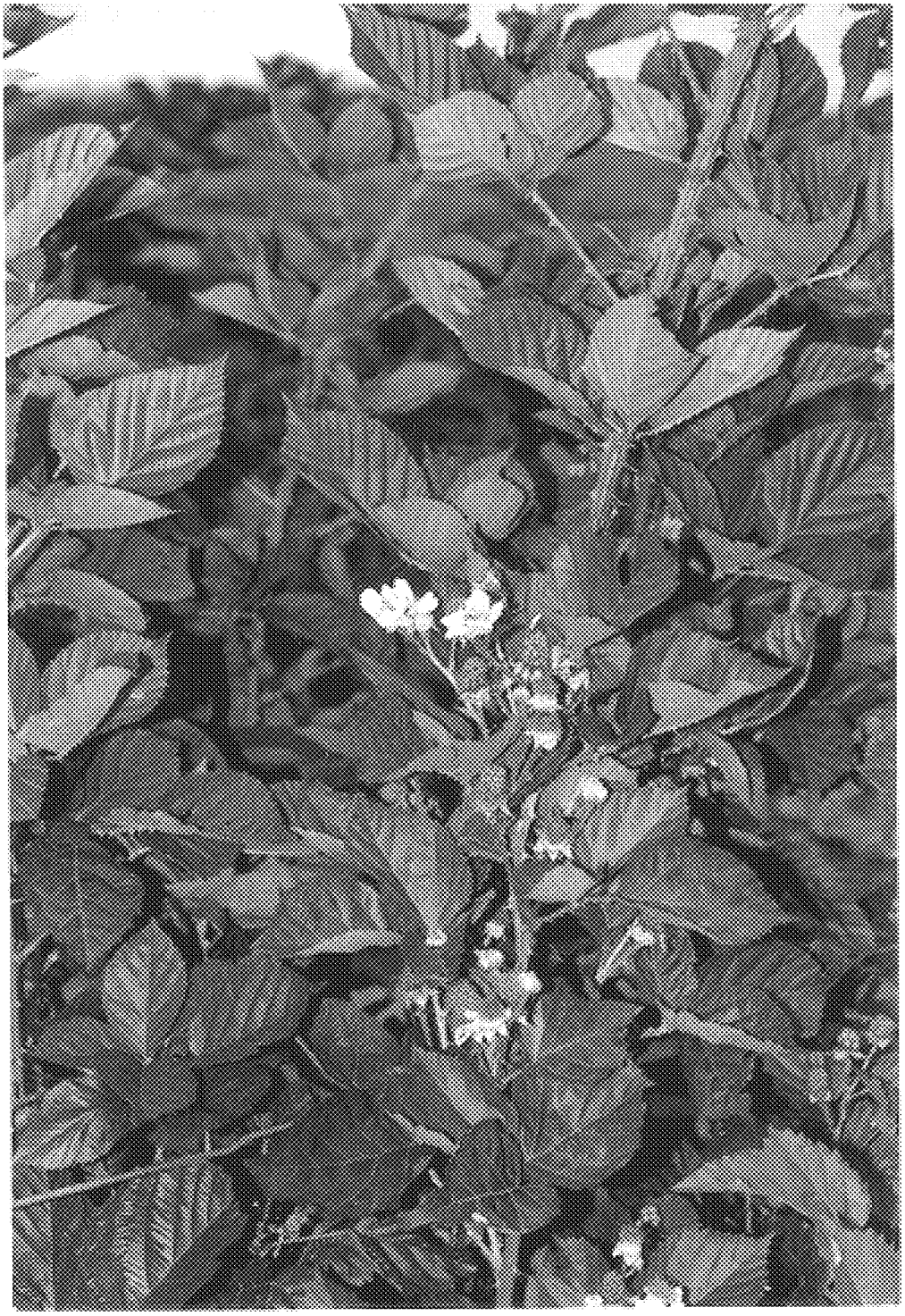
FIG. 3 shows a 'Chesapeake' flowering truss, leaves and the midsection of a 'Chesapeake' primocane.

In the growing season, primocane thorns are moderate in density, 5 mm in length and 3.5 mm diameter at their base, sometimes recurved basipetally and light red (Royal Horticultural Society plate 59A) at the base, but lighter in color (59 B to 59C) and thinner at their apex (see FIG. 2). The red coloration does not extend into the surrounding cane. Pimocane and floricane leaf adaxial surfaces are dark green, most closely in hue to Royal Horticultural Society Color plate 137A, while the abaxial surface of the leaf is pubescent giving this surface a greyer color (Royal Horticultural Society plate 147B)(see FIGS. 2 and 3). Leaves are trifoliate to quinquefoliate and average 14 cm from the distal end of the petiole to the distal end of the terminal leaflet. Leaves have typical blackberry venation patterns with a central vein and several branched side veins; however, puckering due to veins is somewhat less than other eastern blackberry cultivars. This results in relatively flat leaf laminae. The basal leaflets average 14 cm from terminal point to point, i.e. opposing leaves below the terminal leaf, on the petiole average 14 cm from terminal point of the first leaf to the terminal point of the second leaf. The petiole is 5 cm in length and the same light green color as the cane, Royal Horticultural Society plate 143B. Leaf serration is common for most cultivars of blackberry and cannot be used to distinguish this cultivar.

'Chesapeake' floricanes suffer cold injury in mid winter if temperatures fall below 0° F. Floricanes are not truly exfoliating under conditions tested and the floricanes are purple-brown by mid-winter, resembling Royal Horticultural Society plate 178A. Canes can flower from all live buds in April to May depending on latitude, and fruit from mid June to late July in the eastern U.S. This ripeness period is 1–2 weeks later than 'Hull Thornless' (unpatented) and 'Navaho' (U.S. Plant Pat. No. 8,510), but overlaps 'Chester Thornless' (unpatented) and 'Kiowa' (U.S. Plant Pat. No. 9,861).

Figure 4:
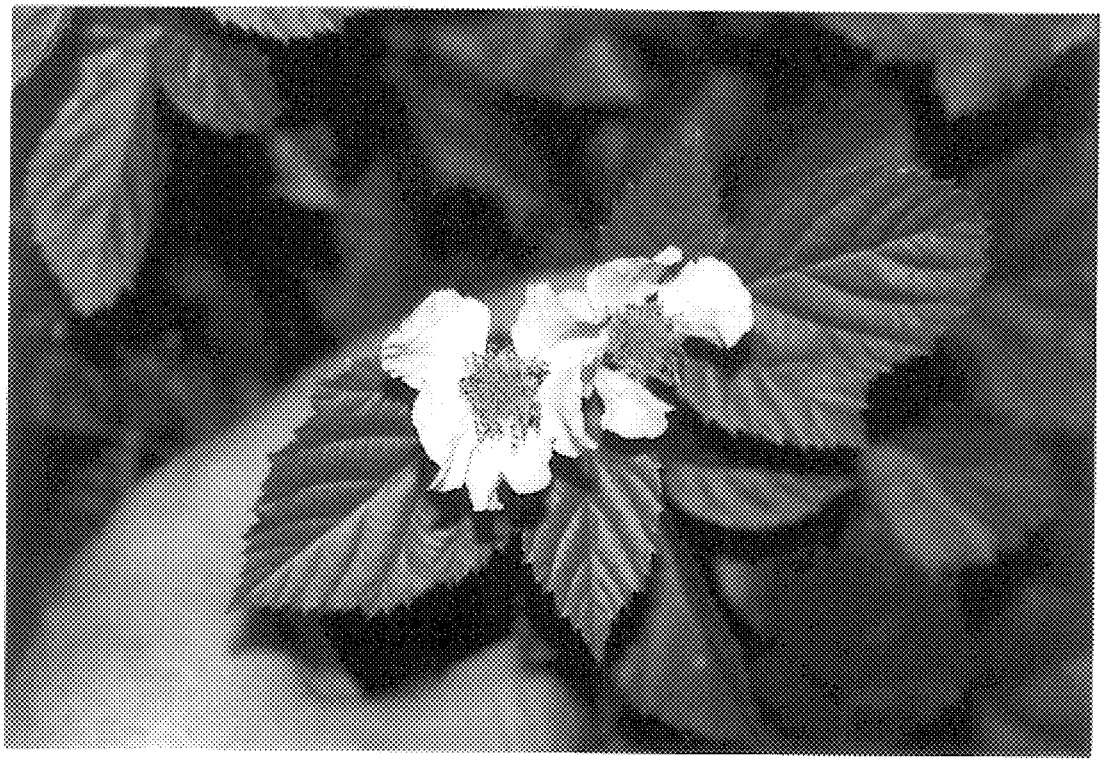
FIG. 4 shows typical 'Chesapeake' flowers.

The flower morphology and early fruit morphology is typical of most eastern U.S. originated blackberry cultivars (the flowers are unscented, 5 white petals 1 to 2 cm long with color resembling Royal Horticultural Society plate 155D, with a slight pink shading on the opening flower resembling Royal Horticultural Society Plate 62C; 5 sepals, resembling Royal Horticultural Society plate 147B and 3 cm long and which cannot be used to identify 'Chesapeake' (see FIG. 4). Flower petals abscise within seven days post pollination. Early flowers typically contain approximately 90 anthers and 89 pistils. Peduncles are slightly hairy and have the same color as primocanes, Royal Horticultural Society plate 143B, and are armed with thorns similar to primocanes, except less than half the size. Peduncles are typically over 2 cm in length.

Figure 5:
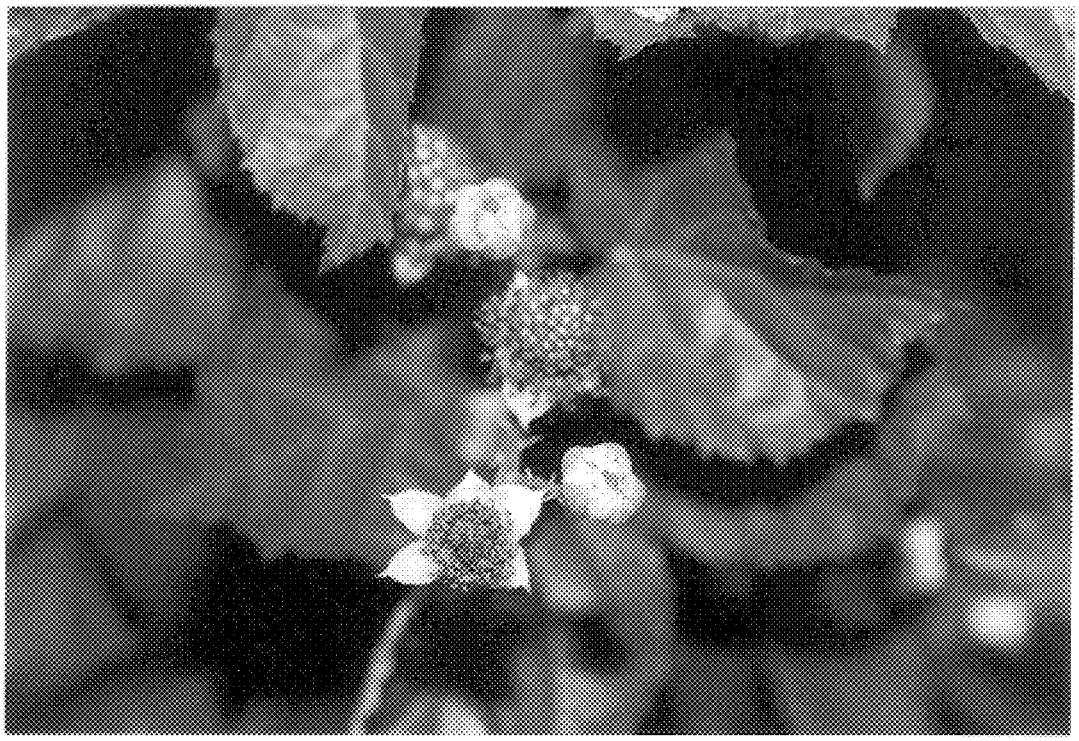
FIG. 5 shows a fruiting cluster of 'Chesapeake', showing unopened flowers through fruit 3 weeks post pollination.
Figure 6:
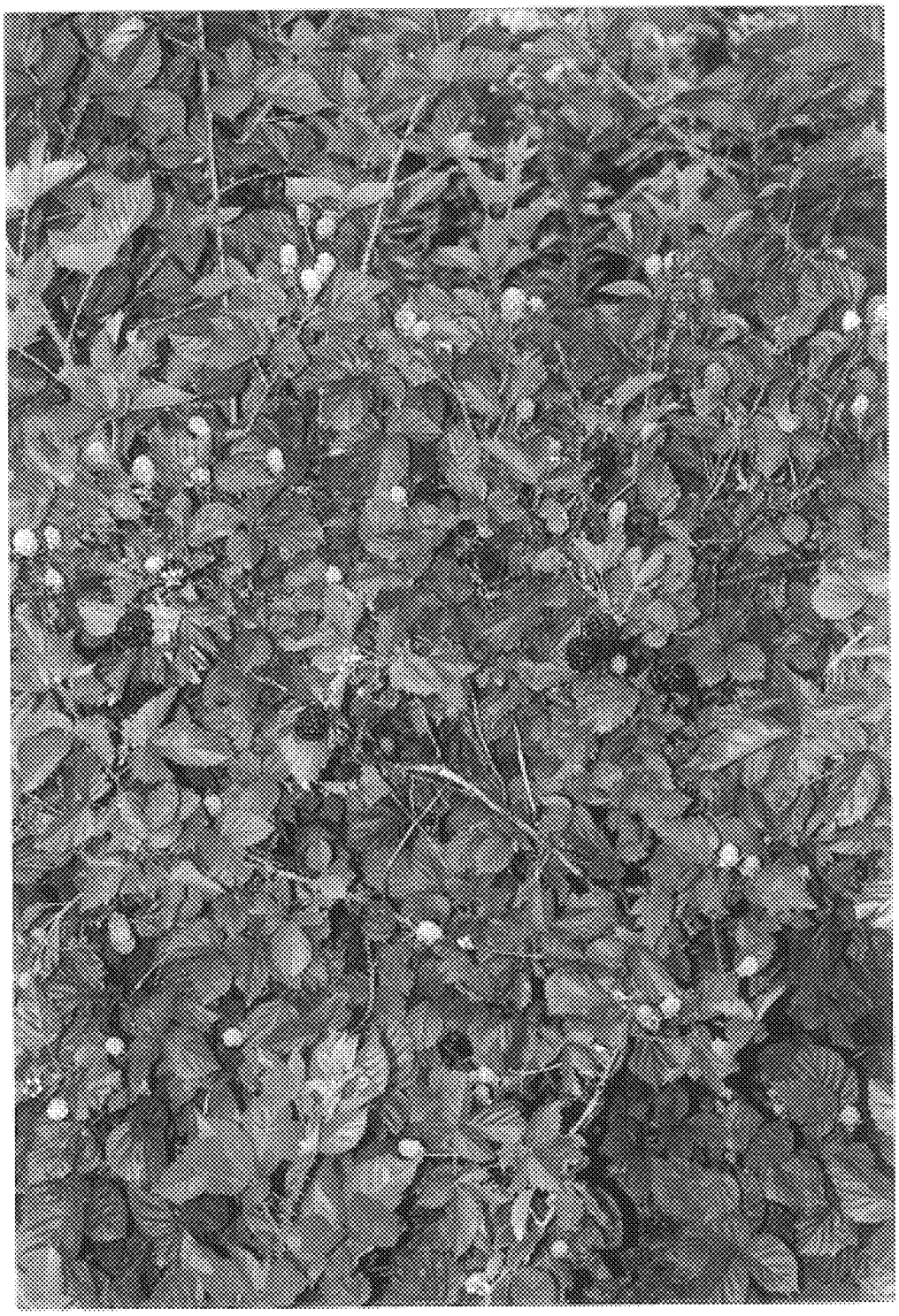
FIG. 6 shows a fruiting cluster of 'Chesapeake' from a two year old plant in Oak Grove, Va.
Figure 7:
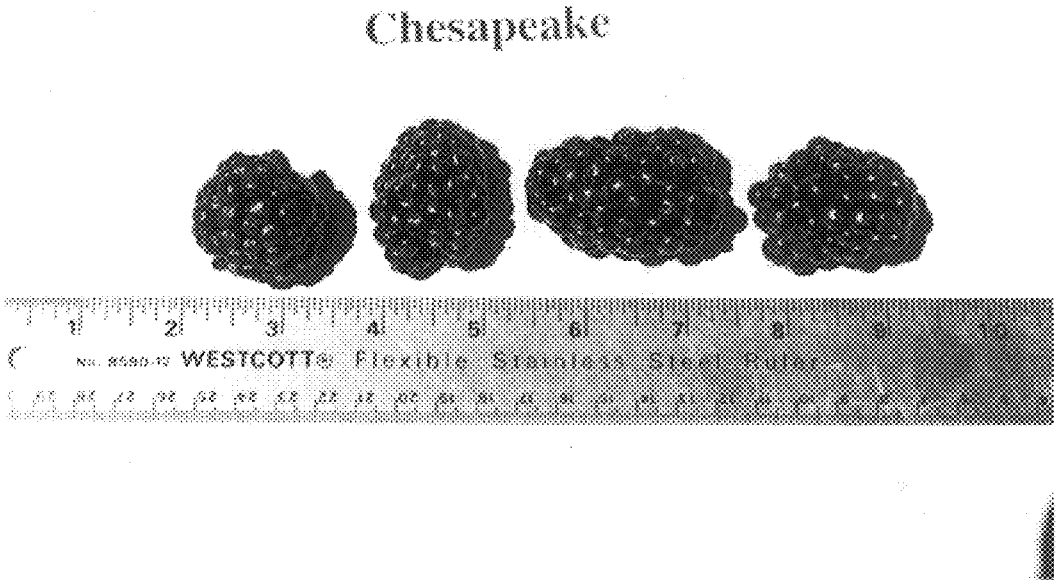
FIG. 7 shows several ripe fruit of 'Chesapeake'.

Fruit trusses are typical cymose clusters with 6 to 15 fruit or more well spaced out on a truss axis (see FIGS. 5 and 6). Twenty-five days after pollination, fruit is distinguishable for this variety by its size only; at this point, unripe fruit is light green (Royal Horticultural Society plate 183C). Fruit is dark black internally and externally when ripe, closely resembling Royal Horticultural Society color plate 202A (see FIG. 7). Fruit has little pubescence, producing a glossy appearance. Fruit is decidedly thick elongate (commonly up to 4 cm in length and 2 cm in width), very large (15–22 gram primary fruit) and somewhat asymmetrical due to variation in drupelet placement (see FIG. 7). Drupelets are held together tightly and the fruit does not "crumble". Fruit separates when slightly unripe, but does not abscise prematurely. Fruit skin toughness is less than 'Chester Thornless' (unpatented), but similar to other thorny cultivars such as 'Shawnee' (U.S. Plant Pat. No. 5,686). The fruit is very "juicy" when crushed and the drupelets are relatively large. Seed size, including woody endocarp, is large, averaging 4.6 mg per seed fresh weight. Fruit flavor is sweet, even when the fruit is unripe. The torus separates from the plant and darkens slightly, from white, upon ripening. The fruit does not break down after at least one week in common storage at 40° F.; however, some drupelets will turn dark red upon storage for even a short period of time (<6 hr). This is typical of blackberry fruit grown in warm climates. Flavor is sweet (not acid or tart) even when unripe, and not characteristic of modern eastern blackberry cultivars, which tend to be highly acid when unripe and "tar-like" when ripe and warm. When grown in cooler regions, or during a cooler than normal spring, 'Chesapeake' fruit has an aroma reminiscent of blueberries.

The plant is field resistant to many of the common pests and diseases in the eastern United States, e.g. mildew and *Phytophthora fragarae* root rot and fruit rot, based on field reaction, not in controlled testing. The plant has not had orange rust or verticillium wilt in several years of exposure in the field, but no claim of resistance is made.

'Chesapeake' has been asexually reproduced by tissue culture and field suckering since 1994. Over that period, no off-type of 'Chesapeake' has been observed or reported to us. Thus, it is concluded that 'Chesapeake' is stable and reproduced true to type in successive generations of asexual reproduction. Tissue culture explants originated from lateral bud meristems and multiplication medium contained 3 to 10 micromolar benzyl adenine. Plants were propagated at South Deerfield, Mass., Hurlock, Md. and the Department of Natural Resource Sciences, University of Maryland, College Park, Md.

What is claimed is:

1. A new and distinct thorny blackberry plant known as 'Chesapeake' as described herein, illustrated and identified by the characteristics set forth above.

* * * * *